(12) United States Patent
Byon

(10) Patent No.: US 7,118,527 B2
(45) Date of Patent: Oct. 10, 2006

(54) PORTABLE ELECTRONIC PENILE ANEURYSM ENHANCER

(76) Inventor: Kyung-Sam Byon, B-102 Koong-jun Village, 1644-7 Bongcheon-dong, Gwanak-gu, Seoul, 151-061 (KR)

( * ) Notice: Subject to any disclaimer, the term of this patent is extended or adjusted under 35 U.S.C. 154(b) by 0 days.

(21) Appl. No.: 10/521,430

(22) PCT Filed: Jul. 8, 2003

(86) PCT No.: PCT/KR03/01334

§ 371 (c)(1),
(2), (4) Date: Nov. 21, 2005

(87) PCT Pub. No.: WO2004/004610

PCT Pub. Date: Jan. 15, 2004

(65) Prior Publication Data

US 2006/0089572 A1   Apr. 27, 2006

(30) Foreign Application Priority Data

Jul. 9, 2002  (KR) .................. 10-2002-0039753

(51) Int. Cl.
*A61F 5/00* (2006.01)
(52) U.S. Cl. ..................................... 600/38; 601/11
(58) Field of Classification Search ............ 600/38–41; 601/6–14
See application file for complete search history.

(56) References Cited

U.S. PATENT DOCUMENTS 4,718,411 A * 1/1988 Stewart ..................... 600/38
4,856,499 A * 8/1989 Kelly ....................... 600/38
5,462,514 A * 10/1995 Harris ..................... 600/38
5,823,991 A * 10/1998 Shim ...................... 604/500
5,836,864 A * 11/1998 Clark, Jr. .................. 600/38

* cited by examiner

*Primary Examiner*—John P. Lacyk
(74) *Attorney, Agent, or Firm*—Blakely, Sokoloff, Taylor & Zafman; Stephen M. De Klerk

(57) ABSTRACT

The present invention is related to an electronic penile aneurysm enhancer and more specifically, a portable electronic penile aneurysm enhancer having a small size to be easily carried around, and by electronically performing expansion and contraction movement of penile muscles, the enhancer invigorates the blood flow movement of spongy body so as to recover the narrowed blood vessels to be normal or so as to penetrate the blocked blood vessels. The present invention comprises a body portion (2); a piston pumping portion (6) provided inside the body portion (2) for pumping to move air through an inlet valve port (12) and an outlet valve port (14); a first electronic three way valve (10) connected to the inlet valve port (12) of the piston pumping portion (6) for converting flow path so as to suck air in; a second electronic three way valve (20) connected to the outlet valve port (14) of the piston pumping portion (6) for converting flow path of the sucked-in air, wherein the penile/male member is expanded and contracted by the first and second electronic three way valves (10, 20). The present invention also comprises a circular enhancing tube (30) having a penile insertion hole (42) and a penile sealing section (40) for expanding and contracting the penis by operating the first and second electronic three way valves (10, 20), and a central control section for controlling the first electronic three way valve (10), the second electronic three way valve (20) and the piston pumping portion (6).

3 Claims, 2 Drawing Sheets

PORTABLE ELECTRONIC PENILE ANEURYSM ENHANCER

CROSS-REFERENCE TO OTHER APPLICATIONS

This is a National Phase of International Application No. PCT/KR2003/001334, filed on Jul. 8, 2003, which claims priority from Korean Patent Application No. 10-2002-0039753, filed on Jul. 9, 2002.

TECHNICAL FIELD

The present invention is related to an electronic penile aneurysm enhancer and more specifically, a portable electronic penile aneurysm enhancer having a small size to be easily carried around, and by electronically performing expansion and contraction movement of penile muscles, the enhancer invigorates the blood flow movement of spongy body so as to recover the narrowed blood vessels to be normal or so as to penetrate the blocked blood vessels.

BACKGROUND ART

In general, penis, the male sexual contact organ can be divided into three parts, penile muscle, penile body and glans.

Penis is an erectile tissue comprising two penile spongy bodies, one urethral spongy body, and a glans which is the expanded part of the front of the urethral spongy body.

In the inner wall of these spongy bodies, there are many pillars composed of connective tissues and smooth muscles intersecting each other to form a net shape, whose structure is similar to that of a sponge because a great number of small spaces such as penile spongy body blocks and urethral spongy body blocks are formed by these intersections. These spongy body blocks, which are a kind of vertical arteria are connected to each other, and are always filled with blood because arteria flows in and vena flows out through spongy body blocks.

When the blood vessels of these spongy body blocks are blocked or narrowed by any reason, normal blood flow movement is interrupted.

Therefore, recently, a hand-operated appliance is being developed in order to overcome such disadvantage; however, because the appliance must be operated by the user manually it does not have any remarkable effect.

DISCLOSURE OF THE INVENTION

The present invention is directed to overcome the above disadvantage of prior art.

It is an object of the present invention to provide a portable electronic penile aneurysm enhancer invigorating the blood flow movement of spongy body by electronically performing expansion and contraction movement of penile muscles so as to recover the narrowed blood vessels to be normal or so as to penetrate the blocked blood vessels.

To obtain the above object, the portable electronic penile aneurysm enhancer comprises a body portion; a piston pumping portion provided inside the body portion for operating pumping to move air through an inlet valve port and an outlet valve port; a first electronic three way valve connected to the inlet valve port of the piston pumping portion for converting flow path so as to suck air in; a second electronic three way valve connected to the outlet valve port of the piston pumping portion for converting flow path of the sucked-in air; a circular enhancing tube having a penile insertion hole and a penile sealing section for expanding and contracting penile by operating the first and second electronic three way valves; and a central control section for controlling the first electronic three way valve, the second electronic three way valve and the piston pumping portion.

The portable electronic penile aneurysm enhancer of the present invention comprising the above will be described in more detail in the following.

The electronic penile aneurysm enhancer of the present invention comprises a piston pumping portion 6 equipped with a motor 4 provided inside the body portion 2.

The piston pumping portion 6 moving air by the pumping of the piston pumping portion 6 which undergoes rectilinear oscillating motion by the operation of a motor 4, is designed to suck air in through an inlet valve port 12 and to discharge the sucked-in air through an outlet valve port 14.

A first electronic three way valve 10 and a second electronic three way valve 20 are designed to convert the flow path of the air sucked-in and discharged by the operation of the piston pumping portion 6.

The first electronic three way valve 10, the second electronic three way valve 20, and the piston pumping portion 6 convert the flow path of air, to expand and contract the penis inserted into the circular enhancing tube 30.

The first electronic three way valve 10, the second electronic three way valve 20, and the circular enhancing tube 30 are connected to each other by a T-shaped connecting tube 25, and the first electronic three way valve 10, the second electronic three way valve 20, and the piston pumping portion 6 are connected to each other by connecting tubes 21 and 23, respectively.

A circular enhancing tube 30 comprises a penile sealing section 40 having a penile insertion hole 42 so as to prevent the outflow of air when the penis is inserted therein.

Further, a safety valve 38 is located at one end of the circular enhancing tube 30 so as to release the inner vacuum pressure when the appliance is malfunctioning.

The penile sealing section 40 is made of a smooth material having elasticity such as silicon because it should expand along with the penis when the penis is inserted and it expands.

A central control section 100 is designed to control the first electronic three way valve 10, the second electronic three way valve 20 and the piston pumping portion 6, which are operated so as to expand and contract the inner air of the circular enhancing tube 30.

Further, the enhancer comprises a power section 106 conveying power to the central control section 100 and other sections; a switch section 102 operating the piston pumping portion 6; an LED section 104 and display section 108 notifying the overall operating status which is controlled by the central control section 100.

BEST MODE FOR CARRYING OUT THE INVENTION

The function and operation of the portable electronic penile aneurysm enhancer of the present invention comprised as above will be described in more detail in the following with reference to the accompanying drawings.

Figure 1:
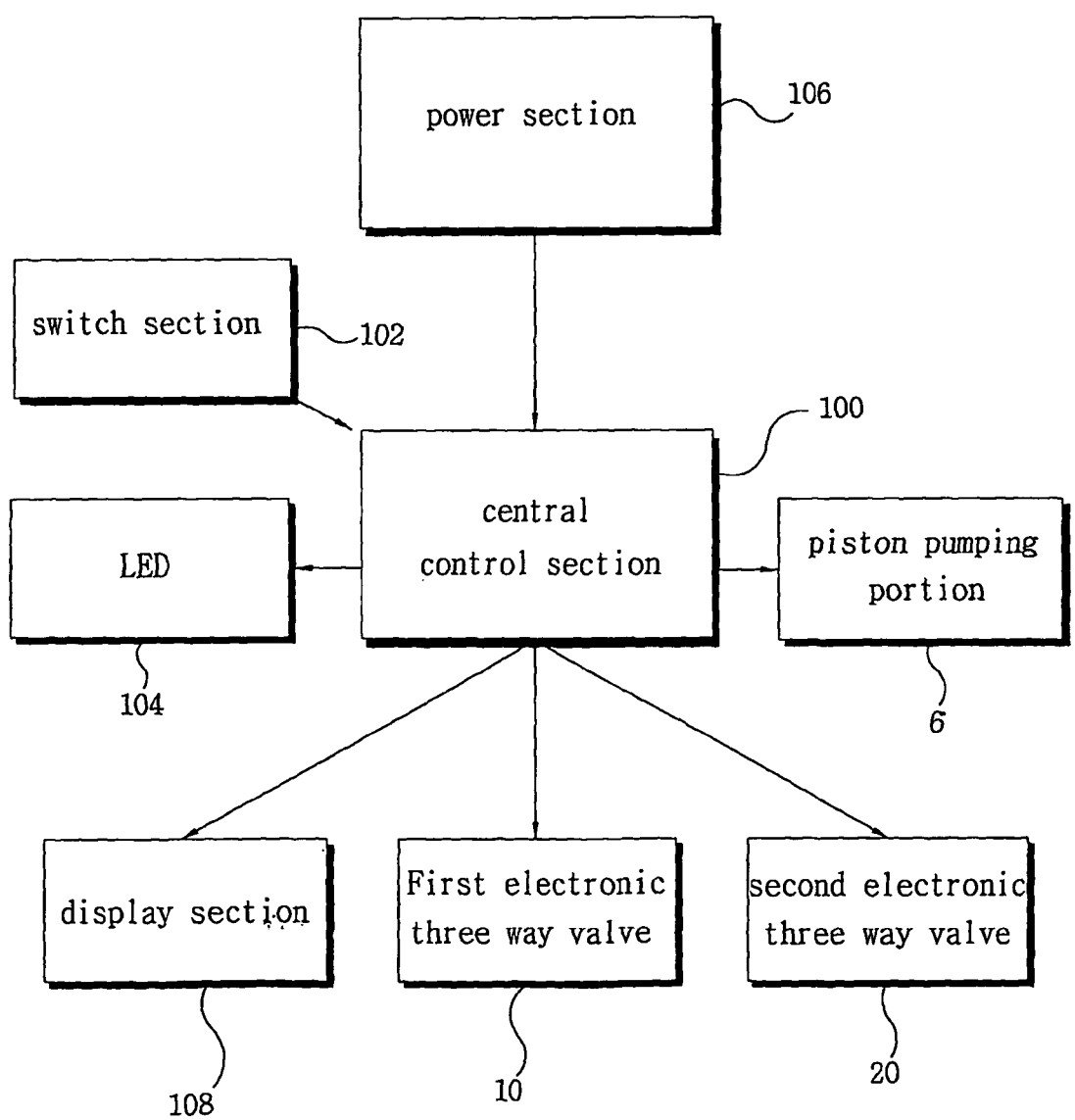
FIG. 1 is a block diagram illustrating the portable electronic penile aneurysm enhancer of the present invention.
Figure 2:
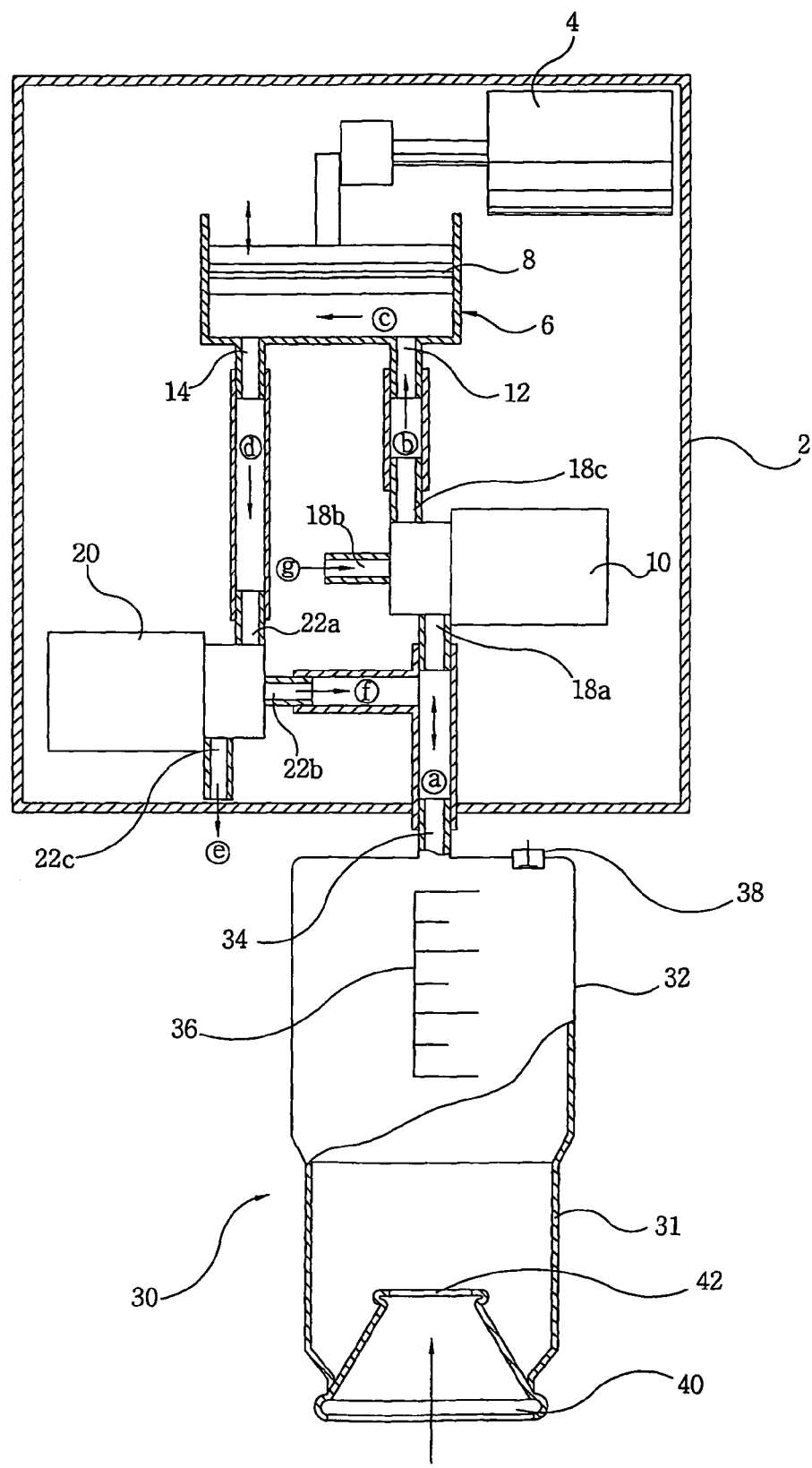
FIG. 2 is a drawing illustrating the portable electronic penile aneurysm enhancer of the present invention.

FIG. 1 is a block diagram illustrating the portable electronic penile aneurysm enhancer of the present invention, and FIG. 2 is a drawing illustrating the portable electronic penile aneurysm enhancer of the present invention.

The penile aneurysm enhancer of the present invention is operated once the user releases power from the power section 106 and presses the requisite switch (on-switch, midway switch, off-switch) of the switch section 102, thereafter.

Then, the piston pumping portion 6 is operated and the circular enhancing tube 30 is operated, accordingly. Hereupon, the penis inserted into the penile insertion hole 42 is gradually sucked in up to the length measuring portion 36 marked up on the circular enhancing tube 30.

The on-switch is operated until the penis reaches the upper part of the circular enhancing tube 30.

The penile sealing section 40 is made of silicon so as to enable it to expand and contract according to the size of the penis. Accordingly, it is completely sealed so as to prevent the inflow of outer air when the penis is inserted.

The enhancer is controlled by the central control section 100 so as to recover narrowed blood vessels to be normal or so as to penetrate blocked blood vessels by performing expansion and contraction movement of the inner air of the circular enhancing tube 30 regularly and repetitively where the penis is inserted.

The central control section 100 may be controlled by a memory device wherein the movement frequency is stored or a micom so as to perform expansion and contraction movement of the penile inserted into the circular enhancing tube 30, repetitively.

Further, the enhancer can be operated by an on-switch of the switch section 102 which only expands the penis; a midway switch of the switch section 102 which automatically performs expansion and contraction movement of the penis at the same time; and an off-switch of the switch section 102 which contracts the penis so that it can be released from the circular enhancing tube 30. In addition, the enhancer comprises an LED section 104 notifying its overall operating status as each switch is operated so that the user can be aware of which operating step is in progress.

Also, the enhancer comprises a display section 108 automatically displaying the time of the penis inserted into the circular enhancing tube 30 performing expansion and contraction movement for 0–180 seconds.

The piston pumping portion 6 starts operating when the on-switch of the switch section 102 shown in FIG. 1 is pressed. Then, the motor 4 shown in FIG. 2 is operated and the piston 8 starts the up-and-down oscillating motion.

When the piston 8 starts oscillating motion as above, the inlet valve port 12 and the outlet valve port 14 of the piston pumping portion 6 start sucking air in and discharging air out, to move the inner air of the circular enhancing tube 30. Thus, the inside of the circular enhancing tube 30 becomes vacuum as sucking in the penis inserted into the penile insertion hole 42.

When air is sucked in through the inlet valve port 12 during the oscillating motion of the piston 8, the direction of the air movement goes through an air passage 34 formed on one end of the circular enhancing tube 30. That is, as shown in FIG. 2, air flows through the air passage 34 formed on one end of the circular enhancing tube 30 following the arrows a, b, c, d, e.

At this time, valve ports 18a and 18c of the first electronic three way valve 10 are open and valve port 18b is closed.

Likewise, valve ports 22a and 22c of the second electronic three way valve 20 are open and valve port 22b is closed.

Therefore, when the inner air of the circular enhancing tube 30 is discharged by the piston pumping portion 6, the penis inserted into the upper circular pressing portion 32 and the lower circular pressing portion 31 of the circular enhancing tube 30 expands up to the length measuring portion 36 marked on the upper circular pressing portion 32.

When the penis inserted into the penile insertion hole 42 of the circular enhancing tube 30 expands up to the length measuring portion 36 of the upper circular pressing portion 32, the user may let go off the on-switch of the switch section 102 shown in FIG. 1 to stop the motor 4 operating.

Once the motor 4 stops, the inside of the circular enhancing tube 30 maintains a high vacuum atmosphere, and thus the penis stays expanded.

After the penile expansion step has ended, if the midway switch of the switch section 102 shown in FIG. 1 is pressed, as described above, the enhancer performs expansion and contraction movement of the penis automatically.

The automatic expansion and contraction movement of the inside of the circular enhancing tube 30 is described as below.

When the midway switch of the switch section 102 is pressed, the piston pumping portion 6, the first electronic three way valve 10 and the second electronic three way valve 20 are operated following the command of the central control section 100.

As the piston pumping portion 6, the first electronic three way valve 10 and the second electronic three way valve 20 are controlled by the command of the central control section 100, the inside of the circular enhancing tube 30 performs expansion and contraction movement from 1 to 180 seconds.

At this time, the penis repeats expansion and contraction movement for 100 to 140 times during 180 seconds.

The movement frequency and time are displayed on the display section 108 shown in FIG. 1.

It is preferable for the end of the penis to undergo oscillating motion within 3 to 7 mm of the length measuring portion 36 marked on the upper circular pressing portion 32 of the circular enhancing tube 30.

It is more preferable to perform expansion and contraction movement within 5 mm when the penis is undergoing oscillating motion in the circular enhancing tube 30.

When undergoing oscillating motion by the aneurysm enhancer of the present invention, if the penis is to be contracted in the circular enhancing tube 30, the central control section 100 shown in FIG. 1 controls the first electronic three way valve 10 and the second electronic three way valve 20.

At this time, valve ports 18a and 22c of the first electronic three way valve 10 and the second electronic three way valve 20 are closed, and valve ports 18b and 22b are open. Thus, air flows through the air passage following the arrows, g, b, c, d, f, a. Since air is sucked in the circular enhancing tube 30 in an instant, the penis which has been pulled up is pushed down again and contracted.

On the contrary, if the penis inserted into the circular enhancing tube 30 is to be expanded by being pulled, valve ports 18b and 22b of the first electronic three way valve 10 and the second electronic three way valve 20 are closed, and valve ports 18a, 18c, 22a and 22c are open. Thus, air flows through the air passage following the arrows, a, b, c, d, e. Since the air of the circular enhancing tube 30 is discharged, the penis is pulled up again and expanded. It can be found out that the expansion and contraction movement is performed from 100 to 140 times during the 180 seconds counted on the display section 108 shown in FIG. 1.

After the 180 seconds of oscillating motion in the circular enhancing tube 30, during the seven seconds, valve ports 18a and 22c of the first electronic three way valve 10 and the second electronic three way valve 20 are closed, and valve ports 18c, 18b, 22a and 22b are open. Thus, air flows through the air passage following the arrows g, b, c, d, f, a to the air passage 34 of the circular enhancing tube 30. This raises the air pressure inside the circular enhancing tube 30 so that the penis inserted into the penile insertion hole 42 of the circular enhancing tube 30 can be released.

This is when the off-switch (not shown) of the switch section 102 may be pressed.

When the off-switch of the switch section 102 shown in FIG. 1 is pressed, as described above, the enhancer goes through a process which is reverse to that when the on-switch of the switch section 102 is pressed.

Further, when the central control section 100 is malfunctioning while operating the switch section 102 shown in FIG. 1 or when the enhancer only performs expansion movement due to the malfunction of the first electronic three way valve 10 and the second electronic three way valve 20, the vacuum atmosphere can be removed, if the safety valve 38 is opened manually.

INDUSTRIAL APPLICABILITY

As described above, when the penile spongy body blocks are narrowed or blocked, normal blood flow movement is interrupted and this may cause impotence of the penis or premature ejaculation. In this regard, inserting the penis into a sealed circular enhancing tube so that it rapidly undergoes oscillating motion within 5 mm for 3 minutes by performing expansion and contraction movement may recover the narrowed blood vessels to be normal or penetrate the blocked blood vessels of spongy body blocks for normal blood flow movement. Thus, it is not only effective in preventing impotence of the penis or premature ejaculation, but is also effective in extending and strengthening penile muscles by performing expansion and contraction movement.

The invention claimed is:

1. A portable electronic penile aneurysm enhancer comprising:
   a body portion (2);
   a piston pumping portion (6) provided inside the body portion (2) for pumping to move air through an inlet valve port (12) and an outlet valve port (14);
   a first electronic three way valve (10) connected to the inlet valve port (12) of the piston pumping portion (6) for converting flow path so as to suck air in;
   a second electronic three way valve (20) connected to the outlet valve port (14) of the piston pumping portion (6) for converting flow path of the sucked-in air;
   a circular enhancing tube (30) having a penile insertion hole (42) and a penile sealing section (40) for expanding and contracting the penis by operating the first and second electronic three way valves (10, 20); and
   a central control section for controlling the first electronic three way valve (10), the second electronic three way valve (20) and the piston pumping portion (6).

2. The portable electronic penile aneurysm enhancer according to claim 1, wherein the circular enhancing tube (30) repeats expansion and contraction operation for 100 to 140 times during 180 seconds.

3. The portable electronic penile aneurysm enhancer according to claim 1, wherein the penis inserted into the circular enhancing tube (30) is undergoing oscillating motion within 3 to 7 mm.

* * * * *